(12) United States Patent
Frielinghaus et al.

(10) Patent No.: US 12,402,973 B2
(45) Date of Patent: Sep. 2, 2025

(54) CRANIUM BRACING SYSTEM

(71) Applicant: Brainlab AG, Munich (DE)

(72) Inventors: Nils Frielinghaus, Munich (DE); Sebastian Stopp, Munich (DE); Stefan Hofberger, Munich (DE)

(73) Assignee: Brainlab AG, Munich (DE)

( * ) Notice: Subject to any disclaimer, the term of this patent is extended or adjusted under 35 U.S.C. 154(b) by 322 days.

(21) Appl. No.: 18/024,591

(22) PCT Filed: Sep. 8, 2020

(86) PCT No.: PCT/EP2020/075003
§ 371 (c)(1),
(2) Date: Mar. 3, 2023

(87) PCT Pub. No.: WO2022/053123
PCT Pub. Date: Mar. 17, 2022

(65) Prior Publication Data
US 2023/0320808 A1   Oct. 12, 2023

(51) Int. Cl.
*A61B 90/14* (2016.01)
*A61B 90/10* (2016.01)

(52) U.S. Cl.
CPC ........ *A61B 90/14* (2016.02); *A61B 2090/103* (2016.02)

(58) Field of Classification Search
CPC ......... A61B 90/10; A61B 90/11; A61B 90/14; A61B 2090/037; A61B 2090/103; A61B 2090/3966; A61N 1/0539
(Continued)

(56) References Cited

U.S. PATENT DOCUMENTS

| | | | |
|---|---|---|---|
| 2013/0072879 A1* | 3/2013 | Avery | A61M 5/003 604/189 |
| 2013/0096570 A1* | 4/2013 | Solar | A61B 90/11 606/108 |
| 2017/0007349 A1 | 1/2017 | Solar et al. | |

FOREIGN PATENT DOCUMENTS

| | | |
|---|---|---|
| EP | 0207452 A2 | 1/1987 |
| WO | 2020006660 A1 | 1/2020 |

(Continued)

OTHER PUBLICATIONS

Written Opinion of the International Searching Authority dated May 26, 2021 for Application Serial No. PCT/EP2020/075003, 6 Pages.
(Continued)

*Primary Examiner* — Jocelin C Tanner
(74) *Attorney, Agent, or Firm* — Tucker Ellis LLP

(57) ABSTRACT

A cranium bracing system includes a strut mount adapter and a bracing strut, wherein the strut mount adapter is adapted to connect the bracing strut to a cranium hole base member which is rigidly connected to a patient's cranium. The strut mount adapter includes a first connecting section with one or more engaging members configured to engage with the correspondingly formed cranium hole base member to fixedly connect the strut mount adapter to the cranium hole base member. The strut mount adapter further includes a second connecting section configured to engage with a correspondingly formed connecting section of the bracing strut to connect the strut mount adapter to the bracing strut, and a passage extending through the strut mount adapter and having a first passage opening at the first connecting section and an opposed second passage opening.

15 Claims, 3 Drawing Sheets

(58) Field of Classification Search
USPC .......................................................... 606/130
See application file for complete search history.

(56) References Cited

FOREIGN PATENT DOCUMENTS

WO       2020020432  A1      1/2020
WO       2020020749  A1      1/2020

OTHER PUBLICATIONS

International Search Report dated May 26, 2021 for Application Serial No. PCT/EP2020/075003, 3 Pages.
Office Action received in corresponding EP Application No. 20768568.6, dated Aug. 23, 2024, 4 pages.

* cited by examiner

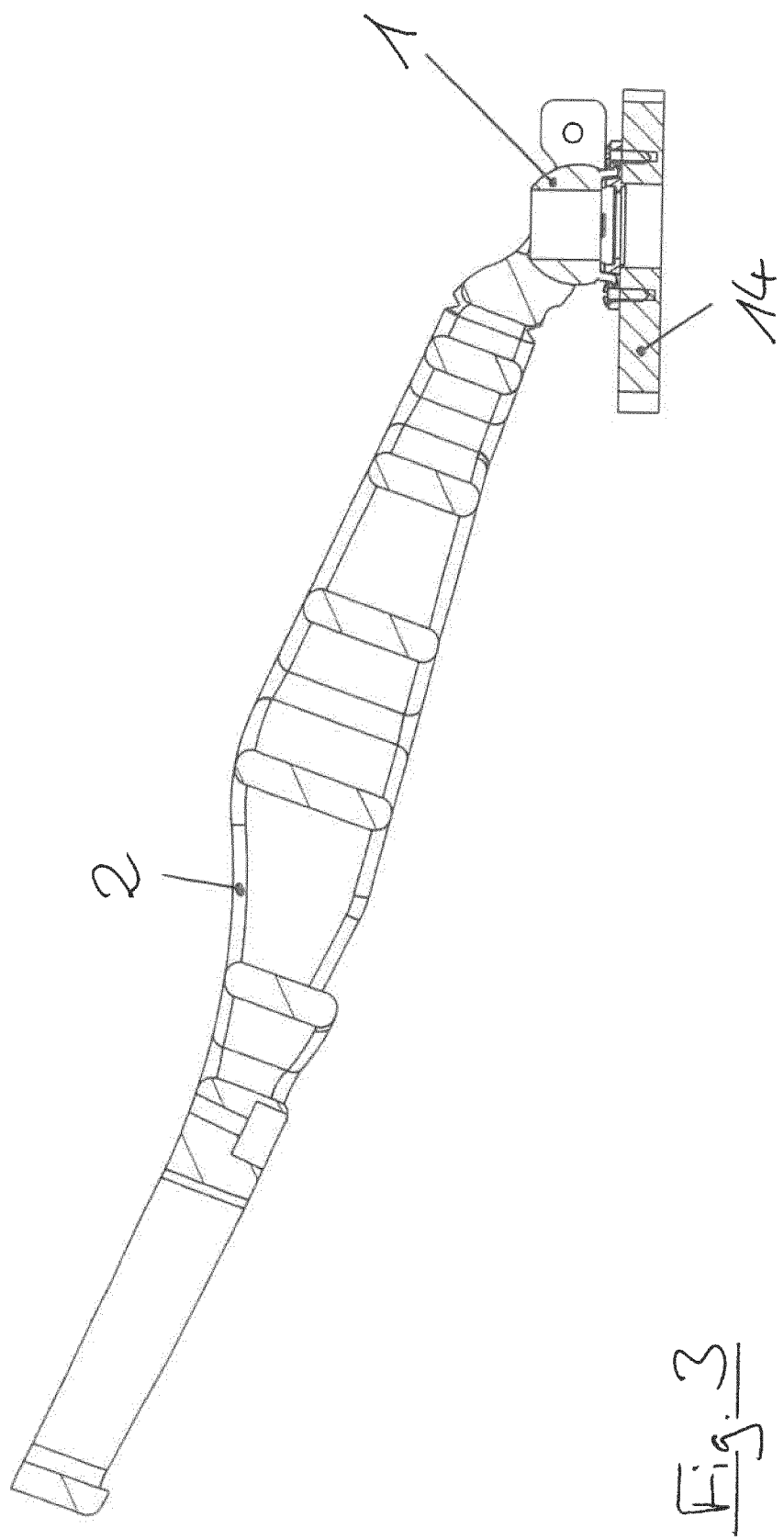

CRANIUM BRACING SYSTEM

RELATED APPLICATION DATA

This application is a National Phase application of International Application No. PCT/EP2020/075003, filed Sep. 8, 2020, filed Sep. 8, 2020, the contents of each of which are incorporated herein by reference.

FIELD

The present invention relates to a bracing system for retaining a patient's cranium in a desired spatial position with respect to medical appliances.

TECHNICAL BACKGROUND

For surgical procedures which are performed on a patient's head, and which may for example include neurosurgical operations that involve placing deep brain stimulation (DBS) electrodes into the patient's brain, it is a fundamental requirement for a successful outcome of the procedure that the patient's head remains in a static spatial position with respect to medical appliances which are used for holding or for guiding instruments and implants with respect to the patient's head.

Previous approaches for holding the patient's head in a fixed spatial position often involve the use of U-shaped head-clamps having several pins which engage the patient's skull and are connected to a heavy mobile trolley. Such trolleys are however bulky and therefore cumbersome and difficult to handle.

Further, US 2016/367331 and WO 2020/020432 suggest systems which connect to a patient's skull via a plurality of adjustable legs and are adapted to guide an elongate medical device along a trajectory with respect to the patient's head.

The present invention has the object of providing an easy to use and inexpensive system which rigidly connects a patient's cranium to medical appliances for holding or guiding surgical instruments and implants, so as to maintain a spatial relative position between the patient's skull and these appliances.

The present invention can be used for surgical procedures performed on a patient's head, for example in the context of deep brain stimulation operations, which may involve the use of a support system for high precision positioning such as Cirq®, a product of Brainlab AG.

Aspects of the present invention, examples and exemplary steps and their embodiments are disclosed in the following. Different exemplary features of the invention can be combined in accordance with the invention wherever technically expedient and feasible.

EXEMPLARY SHORT DESCRIPTION

The present invention relates to a cranium bracing system comprising a strut mount adapter and a bracing strut. The strut mount adapter is configured to connect the bracing strut to a cranium hole base member which is rigidly connected to a patient's cranium while the bracing strut is configured to connect to a medical support structure for holding or guiding surgical instruments and implants, particularly an articulated support arm.

GENERAL DESCRIPTION

In general, the invention reaches the aforementioned object by providing a cranium bracing system comprising a strut mount adapter and a bracing strut, wherein the strut mount adapter includes a first connecting section with one or more engaging members configured to engage with a correspondingly formed solid structure to fixedly connect the strut mount adapter to the solid structure, a second connecting section configured to engage with a correspondingly formed connecting section of the bracing strut to connect the strut mount adapter to the bracing strut, and a passage extending through the strut mount adapter and having a first passage opening at the first connecting section and an opposed second passage opening.

In other words, the inventive bracing system comprises two major parts, namely the strut mount adapter and the bracing strut, which connect to each other in a common interface, particularly via identically shaped surface sections. The bracing structure may further be adapted to connect, for example at a section which is remote from the common interface, to medical appliances such as an articulated support arm. The strut mount adapter on the other hand is further adapted to connect, for example at a section which is remote from the common interface, to a solid structure or object which in turn connects to the patient's cranium. All in all, the bracing strut and the strut mount adapter are adapted to provide a solid interconnection between medical appliances on the one hand and the patient's cranium on the other hand.

In a more specific example, the solid structure may be represented by a cranium hole base member which is adapted to rigidly connect to a patient's cranium, and which includes an access passage to be brought into alignment with a burr hole in the patient's cranium. In particular, the cranium hole base member may further include a connecting section configured to releasably engage with a correspondingly formed cranium hole cover that occludes the access passage.

In a further example, the inventive cranium bracing system includes such cranium hole base member as the correspondingly formed solid structure which is adapted to fixedly connect to the strut mount adapter. Further, the one or more engaging members may be configured to releasably engage with the connecting section of the cranium hole base member, which were initially provided to connect to respective sections of a cranium hole cover.

Further, the strut mount adapter includes a hollow passageway or through-bore that allows an elongate instrument or implant to pass through the strut mount adapter.

In order to provide a maximum possible range of motion for such instruments and implants, the passage may widen at one or both of its openings.

A more specific embodiment of the present invention includes one or more engaging members of the strut mount adapter which are adapted to establish a friction-fit connection, particularly wherein the one or more engaging members include a threaded portion. In a specific example, one or more of the engaging members form a threaded bore or a threaded bolt which may connect to a correspondingly formed thread of the solid structure, such that the strut mount adapter may be connected to the solid structure via one or more threaded connections. In particular, the strut mount adapter may be screwed onto the solid structure and therefore also to the patient's cranium.

Additionally or alternatively one or more engaging members of the strut mount adapter may be configured to establish a form-fit connection. In particular, the one or more engaging members may have resilient properties, i.e. may be elastically deformable. The one or more engaging members may have an undercut portion for establishing a form-fit connection as such undercut portions allow a correspondingly formed solid structure to reach into the undercut portion, thereby holding the engaging members of the strut mount adapter in place. While it is generally conceivable that one or more of the engaging members are rigid (e.g. stiff or dimensionally stable) to engage with elastically deformable sections of the solid structure, one or more of the engaging members may also be elastically deformable to connect to rigid sections of the solid structure. In both of these cases, the strut mount adapter would connect to the solid structure in a so-called "snap-fit"-connection.

In a further example, the one or more engaging members of the strut mount adapter are formed as protrusions that extend from the strut mount adapter. In such case, the strut mount adapter is configured to connect to a solid structure which includes one or more recesses that receive the correspondingly formed engaging members. Alternatively or even additionally, one or more of the engaging members may be formed as recesses adapted to receive correspondingly formed protrusions of the solid structure.

Further, the one or more engaging members may be disposed around the passage, particularly symmetrically and/or in equal distances from each other.

In a further embodiment, the second connecting section of the strut mount adapter and the correspondingly formed connecting section of the bracing strut are configured such that they can be brought into engagement with each other within a predefined range of relative positions of the strut mount adapter and the bracing strut. In other words, the bracing structure can, as long as it takes a position that is within a predefined range of spatial positions with respect to the strut mount adapter, be brought into engagement with the strut mount adapter. For example, this is the case if the strut mount adapter and the bracing strut connect to each other in sort of a ball-joint having a socket-type member receiving a ball-type member. Assuming that the socket-type member has an elastic properties that allow the ball-type member to enter the socket via the socket opening, the corresponding parts of the interface, i.e. the strut mount adapter and the bracing strut can be brought into engagement with each other over a certain range of relative positions between the strut mount adapter and the bracing strut. This is particularly desirable for cases in which the strut mount adapter and the bracing strut are already rigidly connected to the respective structures (i.e. the patient's cranium and the support arm, respectively) before being connected to each other.

Moreover, one of the second connecting section of the strut mount adapter and the correspondingly formed connecting section of the bracing strut may comprise a locking mechanism that is adapted to positionally fix the strut mount adapter and the bracing strut with respect to each other. In other words, the connection between the strut mount adapter and the bracing strut which may initially allow for a relative motion between these elements may be "locked" so as to establish an invariant connection.

Such locking mechanism may for example include a clamping mechanism. In a specific case, a socket-type member may comprise a slotted portion that allows wedging a ball-type member within the socket-type member.

In a further example, the second connecting section of the strut mount adapter may be disposed between the first passage opening and the second passage opening. In other words, the section where the strut mount adapter connects to the bracing strut is passed by the hollow passageway. In a specific example, the second connecting section may radially reach around the passage, particularly may be disposed concentrically with respect to the passage.

In a further example, the second connecting section of the strut mount adapter comprises an at least sectionwise convex surface, particularly an at least sectionwise spherical surface, specifically, a spherical ring surface. On the other hand, the bracing strut comprises a correspondingly formed socket with a concave surface to receive the correspondingly formed strut mount adapter. In particular, the corresponding surfaces may be at least sectionwise identical.

Moreover, the first connecting section and the second connecting section of the strut mount adapter may be configured to be brought into engagement with the solid structure and bracing strut, respectively, in substantially opposed directions. In other words, as seen from the position of the strut mount adapter, the solid structure and the bracing strut are brought into an engagement position with the strut mount adapter by being moved into substantially opposite directions towards the strut mount adapter. In particular, the solid structure may be fitted to the strut mount adapter from "below" the strut mount adapter, whereas the bracing strut is fitted to the strut mount adapter from "above" the strut mount adapter, or vice versa.

In a further embodiment, the first connecting section of the strut mount adapter is configured as snap-in mechanism, such that the strut mount adapter may be snap-fitted to the solid structure. Additionally or alternatively, the same may apply to the connection between the strut mount adapter and the bracing strut.

Further, the strut mount adapter may connect to the bracing strut and/or to the solid structure in a releasable manner. In such case, the respective connections can be disengaged again, for example after the bracing system has been used.

As was already indicated above, the second connecting section of the strut mount adapter may be configured to adjustably engage with its connection section of the bracing strut. In such case, the position of the bracing strut with respect to the strut mount adapter can be re-adjusted as desired before it is fixed to solidly hold the patient's cranium in place.

In a further example, at least one of the strut mount adapter and the bracing strut may comprise a dedicated overload protection section that is adapted to deform or rupture as soon as the load applied to the solid structure via the bracing strut increases a predefined threshold. This preserves the interconnection with the patient's cranium from being overstrained which burdens the risk of bony structures snapping off.

Moreover, the strut mount adapter may comprise one or more radio-opaque fiducials and may therefore serve as marker structure when being connected to the patient's cranium.

A fixed (relative) position and similar expressions in this document means that two objects which are in a fixed position have a relative position which does not change unless this change is explicitly and intentionally initiated. A fixed position is in particular given if a force or torque above a predetermined threshold has to be applied in order to change the position. This threshold might be 10 N or 10 Nm. In particular, the position of a structure remains fixed relative to another structure. A fixed position can for example be achieved by rigidly attaching one object to another. The spatial location, which is a part of the position, can in particular be described just by a distance (between two objects) or just by the direction of a vector (which links two objects). The alignment, which is another part of the position, can in particular be described by just the relative angle of orientation (between the two objects).

BRIEF DESCRIPTION OF THE DRAWINGS

In the following, the invention is described with reference to the appended figures which give background explanations and represent specific embodiments of the invention. The scope of the invention is however not limited to the specific features disclosed in the context of the figures, wherein

FIG. 3 shows a view on the entire bracing system shown in FIG. 1.

DETAILED DESCRIPTION

Figure 1:
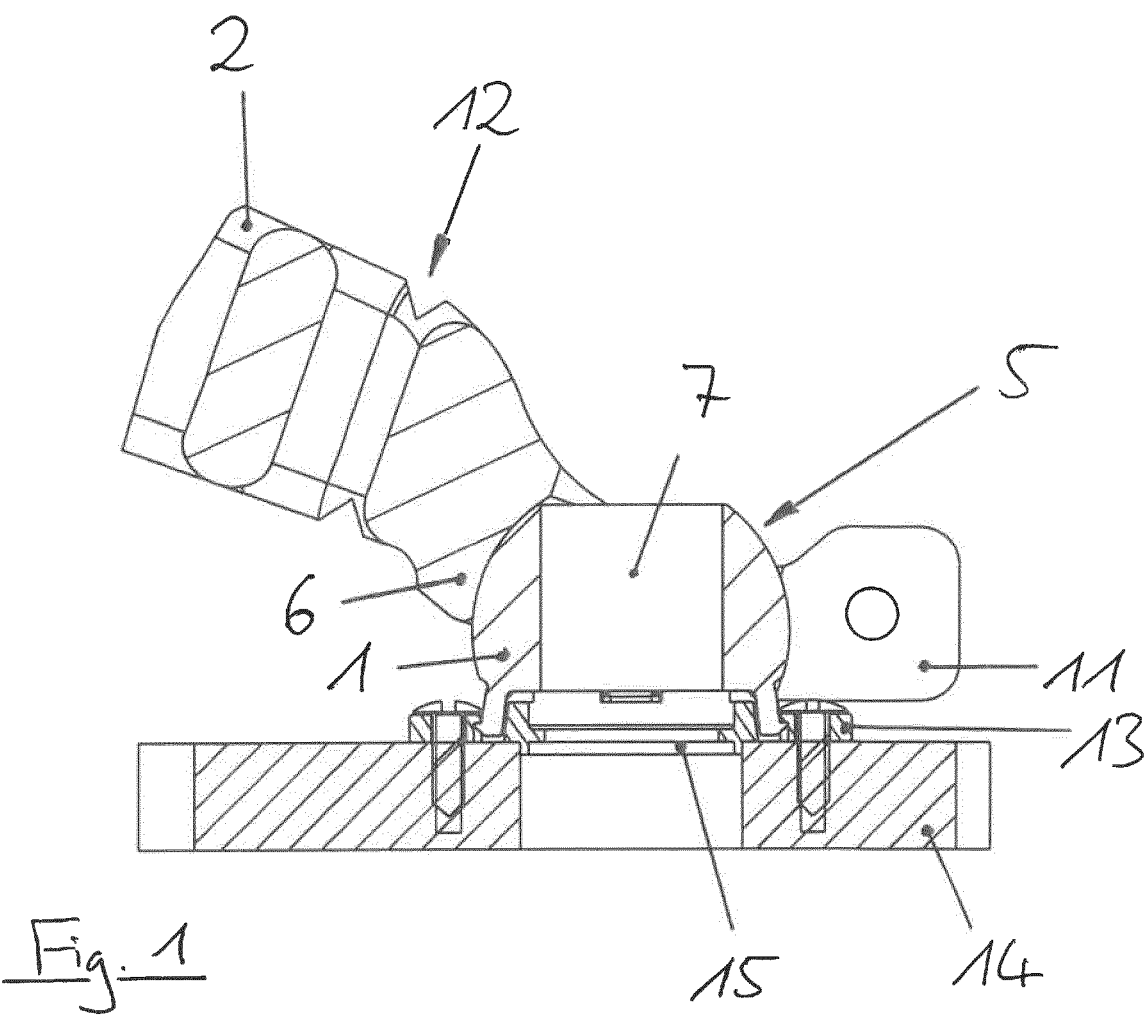
FIG. 1 shows a detailed view on the inventive bracing system.

FIG. 1 shows an exemplary embodiment of the inventive cranium bracing system having a strut mount adapter 1 and a bracing strut 2, which interconnect in a common interface represented by a ball-joint. The strut mount adapter 1 includes a second connecting section 5 having a convex surface that is received by a correspondingly formed concave surface of a connecting section 6 disposed at the distal end of the bracing strut 2. Thus, connecting section 6 forms a socket for a ball-type connecting section 5 of the strut mount adapter 1. The ball-type connecting section 5 is able to enter the socket-type connecting section 6 as the latter has a slotted portion and is therefore resilient, thereby allowing the ball-type connecting section 5 to enter the socket-type connection 6 by passing its tapered bottom opening. Once the bracing strut 2 has been snap-fitted to the strut mount adapter 1 with the ball-type connecting section 5 having entered the socket-type connecting section 6, the relative position between the bracing strut 2 and the strut mount adapter 1 can be set by activating the slotted locking mechanism 11, for example by tightening a bolt-unit-assembly reaching through the bore (not indicated) within the resilient portions of the socket-type connecting section 6, thereby wedging the ball-type connection section 5.

In particular, the ball-type connecting section 5 is reduced to a spherical ring surface with cut off ball-caps at the bottom and the top of the strut mount adapter 1.

Further, a central passage 7 extends through the entire strut mount adapter 1 which allows an elongate instrument or implant to pass through the strut mount adapter 1 and also the bracing strut 2 connected to the strut mount adapter 1 from around the spherical ring surface.

As shown in FIG. 1, the cranium bracing system is held in place with respect to and aligned with a burr hole within a patient's cranium 14 via a substantially ring-shaped cranium hole base member 13 screwed to the patient's cranium 14 such that its access passage aligns with the burr hole. In order to releasably connect the strut mount adapter 1 to the cranium hole base member 13 and the patient's cranium 14, the strut mount adapter 1 includes, at its bottom section 3, four (two of which are shown in the Figures) engaging members 4 evenly distributed around the passage 7 and extending in a downward direction. Each one of the engaging members 4 is formed as a resilient protrusion having an undercut portion 10 disposed above a neck that has a tapered bottom surface and a flat top surface.

Figure 2:
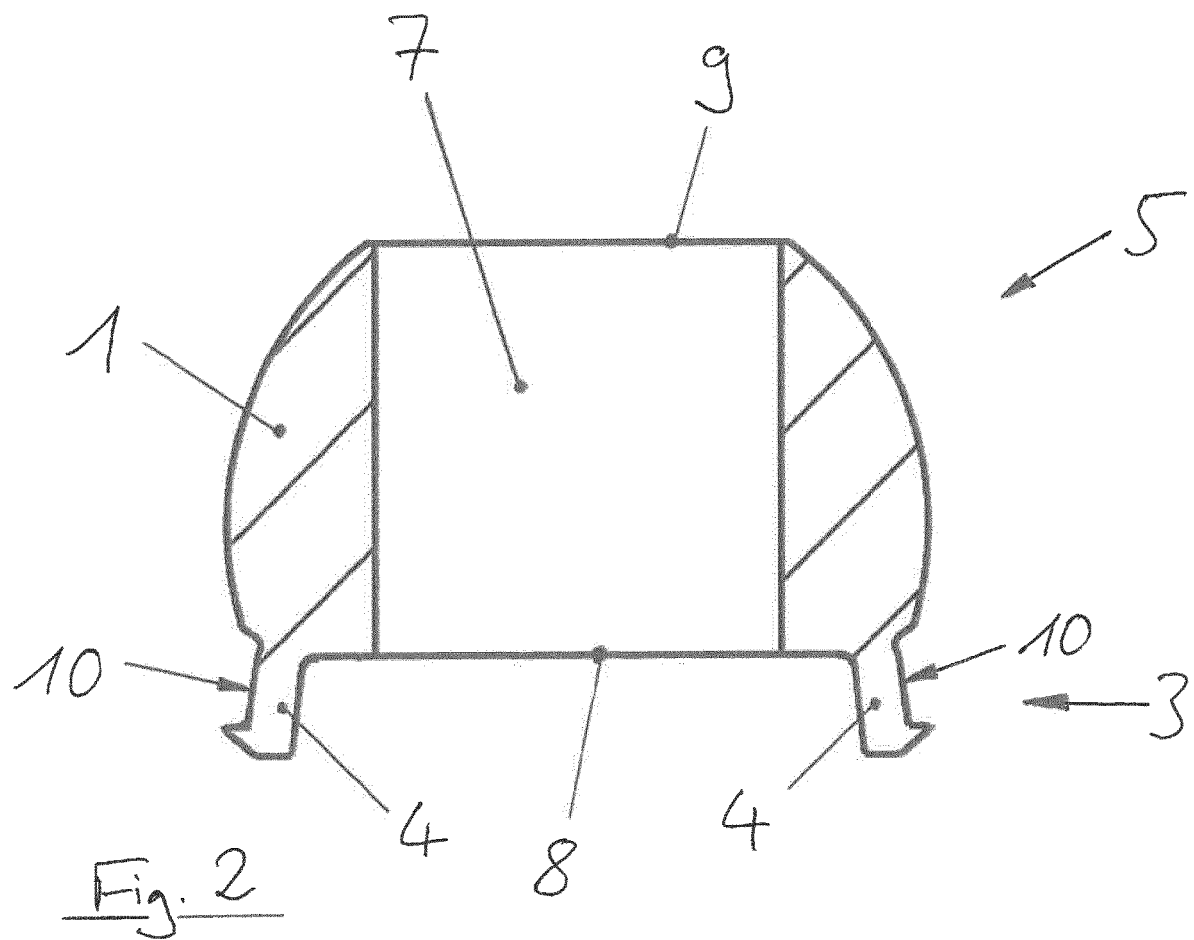
FIG. 2 shows the strut mount adapter of the system shown in FIG. 1.

As becomes apparent from FIG. 2, the resilient engagement members 4 are configured to bend radially inwards as soon as their tapered surfaces contact correspondingly formed recesses of the cranium hole base member 13. As soon as the engaging members 4 have reached their final position within the corresponding recesses of the cranium hole base member 13, they bend radially outwards again to snap-fit into position within the corresponding recesses of the cranium hole base member 13. At this point, the strut mount adapter 1 is fixedly connected to the cranium hole base member 13, but may be removed therefrom again by being pulled upwards with an increased force. Further, the active strut mount adapter 1 is configured as an integrally formed, one-piece member, which may further be provided as a disposable item.

FIG. 3 shows the entire bracing strut 2, which, at its distal portion, connects to the strut mount adapter 1 and is further adapted to connect, at its proximal portion, to medical appliances, for example to an articulated support arm used for holding and/or guiding elongated surgical instruments or implants to pass through the burr hole into the patient's cranium 14. Consequently, as these instruments or implants are held or guided by the same structure to which the bracing strut 2 directly and rigidly interconnects with, the instruments and/or implants are securely held and/or guided with respect to the patient's cranium 14. In order to avoid situations in which the bracing strut 2 applies an excessive load on the cranium hole base member 13, thereby risking the cranium hole base member 13 to snap off from the patient's cranium 14, the bracing strut 2 comprises a dedicated overload protection section, i.e. a constriction 12, at which the bracing strut 2 would break apart in case of an excessive load being applied to the cranium hole base member 13.

The invention claimed is:

1. A cranium bracing system comprising:
   a strut mount adapter; and
   a bracing strut,
   wherein the strut mount adapter includes a first connecting section with one or more engaging members configured to engage with a correspondingly formed associated solid structure to fixedly connect the strut mount adapter to the correspondingly formed associated solid structure,
   wherein the strut mount adapter defines a passage extending through the strut mount adapter, the passage having a first passage opening at the first connecting section and an opposed second passage opening, thereby allowing an elongate instrument or implant to pass through the strut mount adapter,
   wherein the strut mount adapter comprises a second connecting section having an at least sectionwise spherical surface that surrounds the passage,
   wherein the bracing strut comprises a connection section defining a concave surface configured to engage with the second connecting section of the bracing strut mount adapter, wherein the concave surface and the second connecting section are correspondingly formed, to mutually connect the strut mount adapter with the bracing strut.

2. The cranium bracing system according to claim 1, wherein:
   the one or more engaging members are configured to establish a friction-fit connection; and
   the one or more engaging members comprise a threaded portion.

3. The cranium bracing system according to claim 1, wherein:
   the one or more engaging members are configured to establish a form-fit connection; and
   the one or more engaging members are elastically deformable and/or comprise an undercut portion.

4. The cranium bracing system according to claim 1, wherein the one or more engaging members protrude from the first connecting section of the strut mount adapter.

5. The cranium bracing system according to claim 1, wherein the one or more engaging members are disposed symmetrically around the passage.

6. The cranium bracing system according to claim 1, wherein the second connecting section and the correspondingly formed connecting section of the bracing strut are configured such that they can be brought into mutual engagement with each other within a predefined range of relative positions between the strut mount adapter and the bracing strut.

7. The cranium bracing system according to claim 1, wherein at least one of the second connecting section and the correspondingly formed connecting section of the bracing strut comprises a locking mechanism adapted to positionally fix the strut mount adapter and the bracing strut with respect to each other.

8. The cranium bracing system according to claim 1, wherein:
the second connecting section is disposed between the first passage opening and the second passage opening; and
the second connecting section and the passage are disposed concentrically with respect to each other.

9. The cranium bracing system according to claim 1, wherein the second connecting section comprises an at least sectionwise convex surface defining a spherical ring surface.

10. The cranium bracing system according to claim 1, wherein first connecting section and the second connecting section are configured to be brought into mutual engagement with the correspondingly formed associated solid structure and the bracing strut, respectively, in substantially opposed directions.

11. The cranium bracing system according to claim 1, wherein:
at least one of the first connecting section and the second connecting section together with the connecting section of the bracing strut are configured as snap-in mechanism.

12. The cranium bracing system according to claim 1, wherein:
the first connecting section and/or the second connecting section are configured to releasably engage with the correspondingly formed associated solid structure and connecting section of the bracing strut, respectively; and/or
the second connecting section is configured to adjustably engage with the connecting section of the bracing strut.

13. The cranium bracing system according to claim 1, wherein at least one of the strut mount adapter and/or the bracing strut comprises a dedicated overload protection section adapted to deform or rupture at a predefined load applied to the correspondingly formed associated solid structure via the bracing strut.

14. A cranium bracing system comprising:
a cranium hole base member adapted to rigidly connect to a patient's cranium and defining an access passage and a connecting section;
a strut mount adapter; and
a bracing strut,
wherein the strut mount adapter defines a first connecting section comprising engaging members configured to selectively engage with the cranium hole base member to selectively fixedly connect the strut mount adapter to the cranium hole base member,
wherein the strut mount adapter defines a passage extending through the strut mount adapter, the passage having a first passage opening at the first connecting section and an opposed second passage opening,
wherein the strut mount adapter comprises a second connecting section defining a spherical ring surface,
wherein the bracing strut comprises a connection section defining a concave surface configured to engage a correspondingly formed second connecting section of the strut mount adapter to selectively connect the strut mount adapter to the bracing strut,
wherein the cranium bracing system is adapted to allow an elongate instrument or implant to pass through the strut mount adapter and the bracing strut connected with the strut mount adapter from around the spherical ring surface,
wherein the connecting section of the cranium hole base member is configured to releasably engage with a correspondingly formed associated cranium hole cover that occludes the access passage defined by the cranium hole base member.

15. The cranium bracing system according to claim 14, wherein the engaging members are configured to releasably engage with the connecting section of the cranium hole base member.

* * * * *